(12) United States Patent
Suzuki et al.

(10) Patent No.: US 6,340,582 B1
(45) Date of Patent: Jan. 22, 2002

(54) PROCESS FOR PREPARING XYLITOL

(75) Inventors: Shunichi Suzuki; Masakazu Sugiyama; Maiko Mori; Yasuhiro Mihara; Kenzo Yokozeki, all of Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 09/509,543

(22) PCT Filed: Oct. 15, 1998

(86) PCT No.: PCT/JP98/04673

§ 371 Date: Apr. 11, 2000

§ 102(e) Date: Apr. 11, 2000

(87) PCT Pub. No.: WO99/20782

PCT Pub. Date: Apr. 29, 1999

(30) Foreign Application Priority Data

| Oct. 17, 1997 | (JP) | 9-285155 |
| Dec. 1, 1997 | (JP) | 9-330445 |
| Dec. 24, 1997 | (JP) | 9-354674 |
| Jan. 21, 1998 | (JP) | 10-009598 |
| Sep. 11, 1998 | (JP) | 10-258961 |

(51) Int. Cl.$^7$ .................................................. C12P 7/18
(52) U.S. Cl. ................... 435/158; 435/170; 435/190; 435/822; 435/823
(58) Field of Search ................ 435/158, 170, 435/822, 823, 190

(56) References Cited

U.S. PATENT DOCUMENTS

| 5,096,820 A | * | 3/1992 | Leleu et al. | 435/158 |
| 5,631,150 A | * | 5/1997 | Harkki et al. | 435/105 |
| 5,846,794 A | * | 12/1998 | Delobeau et al. | 435/158 |
| 6,242,228 B1 | * | 6/2001 | Sugiyama et al. | 435/158 |

FOREIGN PATENT DOCUMENTS

| EP | 0-403-392 A2 | 12/1990 |
| EP | 0-421-882 A2 | 4/1991 |
| JP | 47-13707 | 7/1972 |
| JP | 8-505522 | 6/1996 |

OTHER PUBLICATIONS

Computer Europafull Abstract EP 1065276, Jan. 2001.*
Hiroshi Onishi, et al., Microbial Production Of Xylitol From Glucose, Applied Microbiology, vol. 18, No. 6, Dec. 1969, p. 1031–1035.

* cited by examiner

Primary Examiner—Herbert J. Lilling
(74) Attorney, Agent, or Firm—Oblon, Spivak, McClelland, Maier & Neustadt, P.C.

(57) ABSTRACT

A method for producing xylitol by allowing a microorganism belonging to the *Gluconobacter oxydans* or *Acetobacter xylinum* and having a D-arabitol dehydrogenase activity and a D-xylulose reductase (xylitol dehydrogenase) activity and an ability to convert D-arabitol to xylitol is acted on D-arabitol in a reaction mixture containing a carbon source to produce xylitol.

10 Claims, 2 Drawing Sheets

PROCESS FOR PREPARING XYLITOL

TECHNICAL FIELD

The present invention relates to a method of producing xylitol. Xylitol is useful in the field of food, medicines, and the like.

BACKGROUND ART

The demand for xylitol, which is a sugar alcohol existing in nature, is expected to increase from now on. Xylitol has a lower caloric value than that of sucrose but is sweet as comparable to sucrose. Thus, it is promising as a low caloric sweetener. Furthermore, xylitol is anticariogenic and can be a dental caries-preventing sweetener. Since xylitol does not raise the blood glucose level, it has been used for infusion liquids for treating diabetes.

At present, xylitol is mainly produced in an industrial scale by hydrogenation of D-xylose as described in U.S. Pat. No. 4,008,825. The raw material, D-xylose, can be obtained by hydrolyzing a starting material such as hardwoods, straws, ear stems of corns, crusts of oats, or the other plant-derived materials rich in xylan.

However, D-xylose that is obtained by hydrolyzing the plant materials is disadvantageously expensive because of the high production cost. For example, the yield of the plant material-hydrolyzed product is low, which makes purity of produced D-xylitol low. After the hydrolysis, it is thus necessary to remove the acid used in the hydrolysis and the pigment by the ion exchange treatment. Furthermore, D-xylitol is crystallized to remove other hemicelluloses. Further purification is required to obtain D-xylose that can be used for food. The ion exchange treatment and crystallization results in an increase of the production cost.

In order to solve the above problems, a method of producing xylitol that uses a readily available starting material and that produces a reduced amount of waste matters has been desired. For example, a method of producing xylitol using pentitol as a starting material has been developed. One of the readily available pentitols is D-arabitol that can be produced using yeast (Can. J. *Microbiol.* 31, 1985, 467–471, J. *Gen. Microbiol.* 139, 1993, 1047–1054).

Several methods have been developed for producing xylitol using D-arabitol as a starting material. *Applied Microbiology*, 18, 1969, 1031–1035 reported a method that comprises producing D-arabitol from glucose by fermentation using *Debaryomyces hansenii* ATCC20121, converting D-arabitol thus obtained to D-xylulose using *Acetobacter suboxydans*, and converting D-xylulose to xylitol using *Candida guilliermondii* var. Soya.

EP-A-403392 (applicant: Roquette Freres) and EP-A-421882 (applicant: Roquette Freres) each discloses a method which comprises producing D-arabitol by fermentation using an osmotic pressure-resistant yeast, converting D-arabitol thus produced to D-xylulose using a microorganism belonging to the genus Acetobacter, Gluconobacter, or Klebsiella, reacting xylulose thus obtained with glucose (xylose) isomerase to produce a mixture of xylose and xylulose, and converting the thus-formed xylose/xylulose to xylitol by hydrogenation. These publications also disclose a method of preliminarily concentrating xylose in the xylose/xylulose mixture and converting concentrated xylose to xylitol by hydrogenation.

The above-described method of producing xylitol using the D-arabitol above as a starting material enables a high yield production of xylitol. However, it is disadvantageous in requiring plural reaction steps, which makes the process complicated. Thus, the method is not economically satisfactory.

To solve these problems, the present inventors have discovered microorganisms having an ability to converting D-arabitol to xylitol directly and developed a method for producing xylitol characterized by allowing the microorganism to act on D-arabitol to produce xylitol and collecting it (Japanese Patent Application Nos. 9-285455 and 10-9598). This method is excellent in that it can efficiently convert D-arabitol to xylitol in a simple one-step process by a fermentation method. However, it calls for further improvements in the stability of reaction and yield of xylitol.

DISCLOSURE OF THE INVENTION

An object of the present invention is to provide a method of producing xylitol using D-arabitol as a starting material and the method achieved by a simple process.

The present inventors have analyzed microorganisms having an ability to directly converting D-arabitol to xylitol to elucidate that the conversion reaction involves D-arabitol dehydrogenase activity and D-xylulose reductase (xylitol dehydrogenase) activity and found that addition of a carbon source or NADH (a reduced type nicotinamide adenine dinucleotide) in a reaction of converting D-arabitol to xylitol permits xylitol production with high stability and high yield, thus completing the present invention.

That is, the present invention relates to a method for producing xylitol comprising the step of reacting a microorganism having an ability to convert D-arabitol to xylitol with D-arabitol to produce xylitol, wherein a carbon source or NADH to is added to a reaction system.

The above-described method is more specifically a method in which when the microorganism is a microbial cell, the carbon source is added to the reaction system and when the microorganism is a preparation product of cells, the NADH is added to the reaction system. The microorganism includes those which have an D-arabitol dehydrogenase activity and D-xylulose reductase (xylitol dehydrogenase) activity. Specifically, the microorganism includes those which have an ability of metabolizing a carbon source to produce NADH and more specifically those which belong to the genera Gluconobacter or Acetobacter, and in particular *Gluconobacter oxydans* and *Acetobacter xylinum.*

The carbon source includes sugars, sugar derivatives, alcohols, aldehydes, organic acids and mixtures thereof. More specifically, the carbon source includes glucose, fructose, sucrose, lactose, sorbitol, glycerol, gluconic acid, methanol, ethanol, propanol, isopropyl alcohol, 1,4-butanediol, 2,3-butanediol, formaldehyde, acetaldehyde, propionaldehyde, isobutyraldehyde, glyceraldehyde, formic acid, acetic acid, citric acid, fumaric acid, malic acid, and mixtures thereof.

According to the present invention, xylitol can be produced from D-arabitol as a raw material in high yields by a simple process.

Hereinafter, the present invention will be described in detail.

<1> Microorganisms Having an Ability to Convert D-arabitol to Xylitol

The microorganisms which can be used in the present invention are microorganisms which have an ability to convert D-arabitol to xylitol. Hereafter, those microorganisms which have such an ability are sometimes referred to as "the microorganisms of the present invention." As the microorganisms of the present invention, there are cited those microorganisms which have both a D-arabitol dehydrogenase activity which oxidizes D-arabitol to D-xylitol and a D-xylulose reductase (xylitol dehydrogenase) activity which deoxidizes D-xylulose to xylitol. Further, it is preferred that the microorganisms of the present invention have an ability to metabolize a suitable carbon source to produce NADH.

Specific examples of the microorganisms which have both a D-arabitol dehydrogenase activity and a D-xylulose reductase activity as well as an ability to metabolize a suitable carbon source to produce NADH include those bacteria belonging to the genera Gluconobacter or Acetobacter. The Gluconobacter bacteria include *Gluconobacter oxydans*, and the Acetobacter bacteria include *Acetobacter xylinum*. More specifically, there are cited the following strains:

*Gluconobacter oxydans* ATCC621
*Gluconobacter oxydans* IAM 1839
*Gluconobacter oxydans* IAM 1842
*Acetobacter xylinum* ATCC14851

Note that the microorganisms which can be used in the present invention may be any one that has the both enzyme activities described above but not limited to the above-described microorganisms.

IAM 1839 and IAM 1942 are available to any person from Institute of Molecular and Cellular Bioscience (formerly, Institute of Applied Microbiology), located at The university of Tokyo, Yayoi 1-chome, Bunkyo-ku, Tokyo, Japan.

The microorganisms of the present invention may include mutants obtained by UV irradiation, N-methyl-nitrosoguanidine (NTG) treatment, ethylmethanesulfonate (EMS) treatment, nitrous acid treatment, acridine treatment or the like or genetic recombinants derived by using genetic engineering methods such as cell fusion or genetic recombination.

<2> Elucidation of Reaction Pathway for Conversion Reaction from D-arabitol to Xylitol (1) Observation of time-course of Conversion Reaction from D-arabitol to Xylitol After the microorganisms of the present invention act on D-arabitol, xylitol is produced. In order to increase the efficiency of the present conversion reaction, it has been tried to elucidate a pathway involved in the production of xylitol from D-arabitol.

Using cells of *Gluconobacter oxydans* ATCC621, the conversion reaction from D-arabitol to xylitol has been investigated in detail as shown in Example 1. Upon investigation of time-course of the reaction, at first D-arabitol was consumed rapidly with concomitant production of D-xylulose. Then, production of xylitol was observed.

D-Arabitol and xylitol are epimers whose asymmetric carbon atoms at the 2-position are in an inverted relationship each other; dehydrogenation of the hydroxyl group at the 2-position of D-arabitol or xylitol gives rise to D-xylulose. Therefore, from the results obtained in Example 1, it was expected that the conversion reaction from D-arabitol to xylitol is a reaction which is mediated by D-xylulose and it proceeds in two-step reactions, i.e., a reaction in which the 2-position of D-arabitol is dehydrogenated to produce D-xylulose and a reaction in which the ketone group at the 2-position of D-xylulose is reduced again stereospecifically to produce xylitol. Based on this idea, investigation has been made on the oxidative activity for D-arabitol and reductive activity for D-xylulose which the microorganisms of the present invention could have.

(2) Detection of D-arabitol Dehydrogenase Activity

Investigation has been made on enzymes which participate in the oxidation reaction of D-arabitol by the microorganisms of the present invention. As the dehydrogenases acting on sugar alcohols, there are reports on the existence of mannitol dehydrogenase (Meth. Enzymol., 9 (1966) 147) and sorbose dehydrogenase (Agric. Biol. Chem., 31 (1967) 640) in *Gluconobacter oxydans* and of glucose dehydrogenase (Agric. Biol. Chem., 44 (1980) 1505) in Pseudomonas bacteria. The activity of various membrane-bound type dehydrogenases can be detected by a method using potassium ferricyanide as an electron acceptor.

Investigation has been made on the existence of D-arabitol dehydrogenase activity in the microorganisms of the present invention using cell homogenate prepared from *Gluconobacter oxydans* ATCC621 as shown in Example 2. As a result, D-arabitol dehydrogenase activity was detected by a detection method using potassium ferricyanide as an electron acceptor.

Further, as shown in Example 3, the cell homogenate prepared from *Gluconobacter oxydans* ATCC621 was allowed to act on D-arabitol, and as a result production of D-xylulose from D-arabitol was confirmed.

The above-described results demonstrate that the microorganisms of the present invention have a D-arabitol dehydrogenase activity, which participates in the conversion reaction from D-arabitol to D-xylulose.

Note that the present inventors have found that some microorganisms have an ability to convert D-arabitol to xylitol. Although most of them utilize NAD as a coenzyme in the conversion reaction from D-arabitol to D-xylulose, it is suggested that in those bacteria which belong to the genus Gluconobacter or Acetobacter an oxidized quinone functions as a coenzyme.

(3) Detection of D-xylulose Reductase (D-xylitol dehydrogenase) Activity

Next, investigation has been made on enzymes which would participate in the reduction reaction of D-xylulose by the microorganisms of the present invention. The D-xylulose reductase (D-xylitol dehydrogenase) activity, which reduces D-xylulose to xylitol is known to exist widely in livers of animals (J. Biol. Chem., 225 (1957) 87) and microorganisms (Biochem. Biophys. Acta. 48 (1961) 26, Biochem. Biophys. Res. Commun., 3 (1960) 554) and the like. The dehydrogenase reaction using NAD(H) or NADP(H) as a coenzyme is reversible. However, difference in the amount of NAD(H) or NADP(H) with oxidation and reduction of a substrate can be measured in terms of changes in absorbance at 340 nm to detect the activity of the enzyme.

Investigation has been made as to whether or not a D-xylulose reductase activity exists in the microorganisms of the present invention using a cell-free extract solution prepared from *Gluconobacter oxydans* ATCC621 as shown in Example 4. As a result, a D-xylulose reductase (D-xylitol dehydrogenase) activity requiring NAD(H) as a coenzyme was detected from the cell-free extract solution.

Further, as shown in Example 5, when a cell-free extract solution prepared from *Gluconobacter oxydans* ATCC621 was allowed to act on D-xylulose, production of xylitol was confirmed. Further, in this reaction, the amount of xylitol produced was proportional to the amount of NADH added.

These results demonstrate that the microorganisms of the present invention have a D-xylulose reductase (D-xylitol dehydrogenase) activity and that the conversion reaction of D-arabitol involves the activity of this enzyme.

<3> Enhancement of Conversion from D-arabitol to Xylitol by Addition of a Carbon Source As described above, confirmation of the existence of a D-arabitol dehydrogenase activity and a D-xylulose reductase (D-xylitol dehydrogenase) activity in the microorganisms of the present invention, it has revealed that in the conversion reaction of D-arabitol to xylitol by the action of the microorganisms of the present invention, there proceed a two-step reaction involving a reaction in which D-arabitol is oxidized to be converted to D-xylulose and a reaction in which D-xylulose is reduced again to be converted to xylitol.

In the reaction in which *Gluconobacter oxydans* ATCC621 is allowed to act on D-arabitol to convert it to xylitol, xylitol is produced and accumulated in a relatively high concentration as shown in Example 1. However, the yield is not still satisfactory. To analyze this reaction, the D-arabitol oxidation reaction in the first step proceeded advantageously so that D-arabitol was consumed completely whereas the D-xylulose reduction reaction in the second step did not proceed completely so that a portion of D-xylulose remained unreacted, and the reaction did not proceed further in spite of extension of reaction time. Therefore, it was considered that an increase in the yield of xylitol requires an increase in the efficiency of the D-xylulose reduction reaction in the second step.

As elucidated in <2> (3) described above, the xylulose reductase participating the reduction reaction of D-xylulose of the microorganisms of the present invention requires NAD(H) as a coenzyme and in order to reduce D-xylulose requires NADH in an equimolar amount with respect to D-xylulose. This suggested that the cause why D-xylulose remains unreacted in the conversion reaction from D-arabitol to xylitol is attributed to the deficiency of NADH which is necessary for the reaction.

It was considered if the deficiency of NADH was the cause, generation of NADH by some means would allow the reduction reaction of xylulose to proceed completely so that the yield of reaction could be increased. Since NADH and NADPH act as coenzymes for various oxidoreductases in vivo, it has been well known to reproduce NADH and NADPH from NAD and NADP, respectively, utilizing the metabolism of bacteria. There have been reported a large number of examples of reduction reactions utilizing microorganisms having oxidoreductases which require NADH and NADPH as coenzymes. For example, there can be cited production of (S)-2-hydroxypropylphenylsulfone by asymmetric reduction reaction using yeast (Agric. *Biol. Chem.*, 42 (1978) 451), production of (S)-3-hydroxyvaleric acid by asymmetric reduction reaction using quiescent cells of *Thermoanaerobium brockii* (*Helv. Chim. Acta.*, 68 (1985) 958) and the like. In these reactions, an increase in productivity is obtained by addition of a suitable carbon source together with a substrate which is oxidized upon the reaction.

Therefore, in the production of xylitol from D-arabitol by the microorganisms of the present invention, it is expected that addition of a carbon source which is metabolized by the microorganism produces NADH from NAD according as the carbon source added is metabolized so that the xylulose reduction reaction in the second step can proceed advantageously to increase a yield.

Based on this idea, as shown in Example 6, glucose and ethanol were added and allowed to react in a conversion reaction of D-arabitol using *Gluconobacter oxydans* ATCC621 and the effect of their addition was examined. As a result, a considerable effect of addition was recognized as shown in Example 6. That is, when no carbon source was added, a portion of D-xylulose remained unreacted, giving a low yield of xylitol whereas with the addition of a carbon source, reduction of D-xylulose to xylitol proceeded advantageously and the yield of xylitol (based on the yield of D-arabitol) reached at most 98%.

Even if NADH is produced when a carbon source is metabolized, the produced NADH is immediately used and consumed in D-xylulose reduction reaction so that it is difficult to determine the quantity of NADH produced. However, judging from the participation of D-xylulose reductase activity which requires NADH as a coenzyme in the conversion reaction of D-arabitol by the microorganisms of the present invention and a dependence of the amount of xylitol produced on that of NADH as shown in Examples 4 and 5, it is presumed that NADH is produced from NAD according as the added carbon source is metabolized.

As described above, the present inventors have made analysis on the bacteria which have an ability to directly convert D-arabitol to xylitol and elucidated that D-arabitol dehydrogenase activity and D-xylulose reductase (xylitol dehydrogenase) activity participate in this conversion reaction. Also, the present inventors have found that addition of a carbon source in the conversion reaction from D-arabitol to xylitol permits stable production of xylitol with high yields.

<4> Cultivation Method for Cultivating the Microorganisms of the Present Invention and Production Method for Producing Xylitol Using the Microorganisms Hereinafter, description will be made on the cultivation method for the microorganisms of the present invention and a method for producing xylitol by allowing the microorganisms to act on D-arabitol.

Media for cultivating these microorganisms are not particularly limited and usual media containing usually used carbon sources, nitrogen sources, inorganic ions, and, if necessary, organic nutrients, can be used. As the carbon sources, carbohydrates such as glucose, alcohols such as glycerol, organic acids, or the like can be appropriately used. The nitrogen sources include ammonia gas, aqueous ammonia, ammonium salts, nitrates, or the like. The phosphorus sources include potassium phosphate, sodium phosphate, or the like. As the inorganic ions, magnesium ions, potassium ions, iron ions, manganese ions, sulfate ions, or the like can be appropriately used if required. Suitable organic nutrients include vitamins, amino acids, and liver extract, yeast extract, malt extract, peptone, meat extract, corn steep liquor, casein hydrolyzing products, or the like containing vitamins and amino acids.

Further, it is sometimes the case where addition of sugars or sugar alcohols such as D-xylose, D-xylulose, D-arabitol, D-sorbitol, D-mannitol, xylitol or the like as an inducer in the culture medium enhances the activity of an enzyme which participates in the conversion reaction from D-arabitol to xylitol.

The culturing conditions are also not particularly limited. For example, culturing may be carried out for 12 to 72 hours with controlling the pH value within pH 5 to 8 and the temperature within the 25 to 40° C. under aerobic conditions.

The microorganisms cultured as described above are contacted with D-arabitol to produce xylitol in the reaction mixture. In the method of the present invention, the above-described microorganism may be microbial cells themselves or preparation products of the microbial cells as long as the products are capable of converting D-arabitol to xylitol. Specifically, such preparation products include the culture containing the microbial cells, microbial cells that are separated and recovered from the culture, immobilized products of the microbial cells, the microbial cells treated with acetone, or freeze-dried, cell disrupted solution, fractions or purified enzyme fractions of the cell disrupted solution, and immobilized products of these treated cells.

No particular limitation is posed on the concentration of D-arabitol and usually use of 1 to 50% (w/v), preferably 5 to 40% (w/v), gives good results. Upon the reaction, addition of D-arabitol of substrate, in portions may result in an increased yield. No particular limitation is posed on the reaction conditions, and usually the reaction is ran under aerobic conditions at a reaction temperature of 20 to 60° C., preferably 30 to 40° C., at a reaction pH of 3.0 to 10.0, preferably a pH of 4.0 to 7.0, with good results. The yield of xylitol can sometimes be increased by preventing reduction of the pH value during the reaction by, for example, adding calcium carbonate to the reaction mixture to give a concentration of 2% (w/v). Both of stationary reaction and stirring reaction can be used. The reaction period is preferably from 1 to 100 hours though it varies depending on the conditions such as the activity of the microorganism used or the concentration of D-arabitol.

In the present invention, in order to increase the efficiency of conversion reaction from D-arabitol to xylitol and accumulate xylitol in high yields, a suitable carbon source or NADH is added to the reaction system upon reaction. In the case where cells, particularly living cells, of the microorganism having an ability to metabolize the carbon source to produce NADH are used as a microorganism, addition of a carbon source in the reaction system results in production of NADH from NAD accompanying with the metabolism of the carbon source. As a result, the conversion reaction from D-xylulose to xylitol proceeds smoothly. In the case where treated cell products such as cell homogenates, particularly treated cell products of those bacteria belonging to the genera Gluconobacter or Acetobacter are used, the reduction reaction of D-xylulose can be proceeded efficiently by directly adding NADH to the above-described reaction system.

The above-described carbon source is not particularly limited as far as it is a carbon source which is accompanied by production of NADH upon its metabolization, and includes sugars, sugar derivatives, alcohols, aldehydes, organic acids, and the like. Examples of the sugars include glucose, fructose, sucrose, and lactose. Examples of the sugar derivatives include sugar alcohols such as sorbitol, mannitol, and glycerol, aldonic acids such as gluconic acid, and the like. In addition, examples of the alcohols include methanol, ethanol, propanol, isopropyl alcohol, 1,4-butanediol, 2,3-butanediol, and the like. Examples of the aldehydes include formaldehyde, acetaldehyde, propionaldehyde, isobutyraldehyde, glyceraldehyde, and the like. Examples of the organic acids include formic acid, citric acid, fumaric acid, malic acid, and the like. These carbon sources may be used alone or any two or more of them may be used as mixtures. While the amount of the carbon source to be added may vary depending on the activity of bacterial cells used, the concentration of D-arabitol or the like conditions, good results will be obtained when a total amount is in the range of 0.2 to 40% (w/v), preferably 0.5 to 20% (w/v). The timing of addition of the carbon sources is not limited particularly, and they may be added at the initiation of reaction or during the reaction or in portions.

Xylitol produced in the culture medium as described above is recovered and isolated from the reaction mixture by the conventional methods. Specifically, the solid matter is removed by centrifugation, filtration, or the like method, the resulting liquid fraction is decolored and desalted using activated carbon or an ion-exchange resin, and the desired product is crystallized from the solution.

BEST MODE FOR CARRYING OUT THE INVENTION

The present invention will be illustrated in more detail with reference to examples, but is not to be construed to be limited to the examples. In the following examples, the starting material, D-arabitol, and xylitol produced were analyzed by high performance liquid chromatography (HPLC) under the following conditions:

Column: Shodex SC1211 (product of Showa Denko)

Mobile phase: 50% acetonitrile/50% 50 ppm Ca-EDTA aqueous solution

Flow rate: 0.8 ml/min

Temperature: 60° C.

Detection: RI detector

EXAMPLE 1

Time Course of Conversion Reaction of from D-arabitol to Xylitol by *Gluconobacter oxydans* ATCC621

50 ml of a culture medium (pH7.0) containing 2.4% (w/v) of potato dextrose (manufactured by Difco Co.), 3% of yeast extract (Difco), 0.5% of meat extract (Difco), and 1.5% of glycerol was dispensed in 500 ml Sakaguchi flasks and sterilized at 120° C. for 15 minutes. After a D-arabitol solution was sterilized at 120° C. for 15 minutes, it was added to the above-described culture medium to a concentration of 3.0%. Further, 1 g of calcium carbonate, after sterilized at 200° C. for 120 minutes, was added to the culture medium described above. *Gluconobacter oxydans* ATCC621 was inoculated to this culture medium and cultivated with shaking at 30° C. for 3 days. The bacterial cells were collected from the culture solution by centrifugation and washed once with physiological saline.

Figure 1:
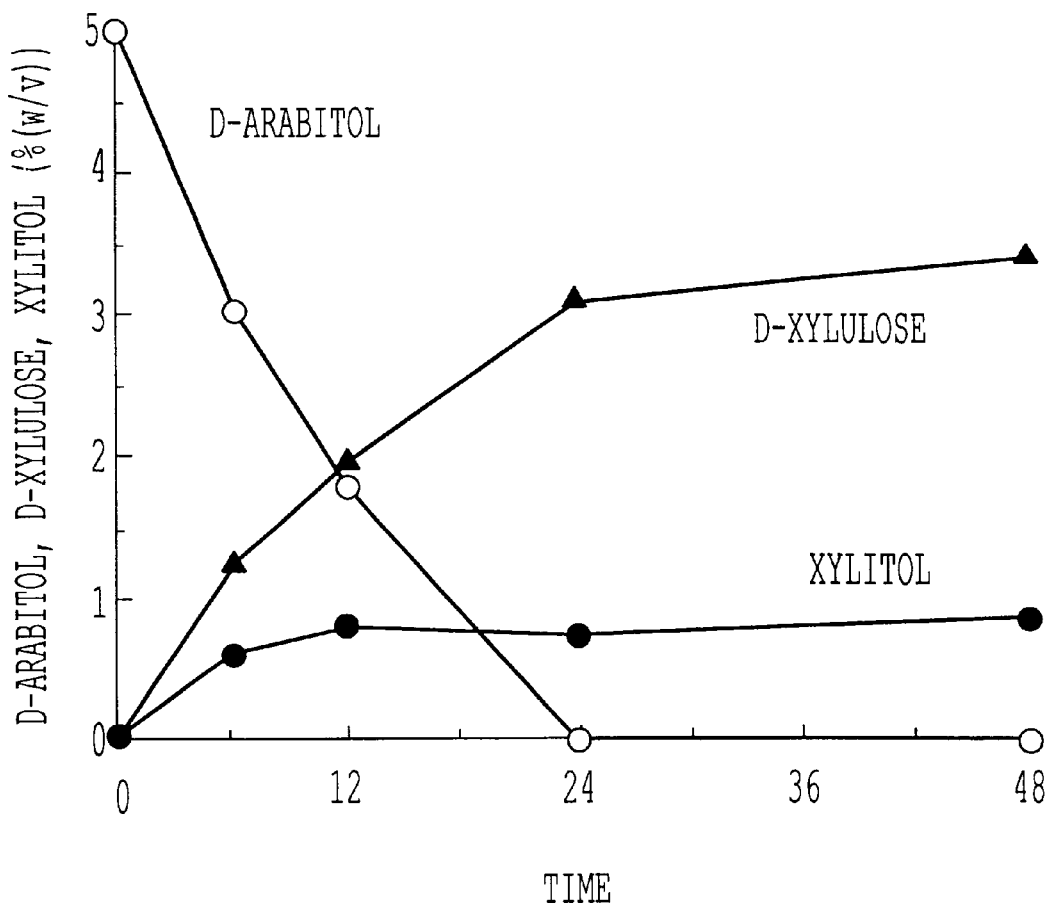
FIG. 1 is a graph illustrating a time-course of a conversion reaction from D-arabitol to xylitol by *Gluconobacter oxydans* ATCC621 cells.

D-arabitol was dissolved in 0.1M phosphate buffer solution(pH 6.0) to a concentration of 5% (w/v), to which the washed cells were added in a wet weight of about 10% (w/v). 10 ml of this reaction mixture was placed in a test tube, and a reaction with shaking was run at 30° C. Each 1 ml sample was taken after 6, 12, 24, and 48 hours from the initiation of the reaction. After removing the bacterial cells by centrifugation, the reaction product was analyzed by HPLC. FIG. 1 illustrates the results.

As illustrated in FIG. 1, at first D-arabitol was rapidly consumed and accompanying this, production of D-xylulose was observed, which however stopped halfway and the reaction did not proceed any further even when the reaction time was extended.

EXAMPLE 2

Detection of Arabitol Dehydrogenase Activity of *Gluconobacter oxydans* ATCC621

50 ml of a culture medium (pH7.0) containing 2.4% (w/v) of potato dextrose (manufactured by Difco Co.), 3% of yeast extract (Difco), and 0.5% of meat extract (Difco) was dispensed in 500 ml Sakaguchi flasks and sterilized at 120° C. for 15 minutes. After a D-arabitol solution was sterilized at 120° C. for 15 minutes, it was added to the above-described culture medium to a concentration of 2.0%.

Further, 1 g of calcium carbonate, after sterilized at 200° C. for 120 minutes, was added to the culture medium described above. *Gluconobacter oxydans* ATCC621 was inoculated to this culture medium and cultivated with shaking at 30° C. for 3 days. The bacterial cells were collected from the culture solution by centrifugation and washed once with physiological saline.

Cultivated bacterial cells of about 1.0 g in wet weight collected from 100 ml of the culture solution was suspended in 10 ml of 0.1M phosphate buffer solution(pH 7.0), and sonicated at 4° C. for 20 minutes to prepare a cell homogenate. The protein concentration of the homogenate was determined by Bradford method (*Anal. Biochem.*, 72, 248 (1976)) using BSA (Bovine Serum Albumin) (manufactured by SIGMA Co.) and Bio-rad protein assay reagent (manufactured by Bio-rad).

According to the method of Iiyama et al. (*Agric. Biol. Chem.*, 42 (1978) 2063) a D-arabitol dehydrogenase activity was measured. The reaction was carried out in a 600 µl reaction mixture containing 10 mM potassium ferricyanide, 100 mM D-arabitol, 100 mM sodium acetate buffer solution (pH 5.0), and 2 µl of cell homogenate at pH5.0 and at 25° C. for 30 minutes. 300 µl of Dupanol reagent (5 g/L iron (III) sulfate n-hydrate, 3 g/L SDS, 95 ml/L 85% phosphoric acid) was added to stop the reaction and 2,100 µl of distilled water was added, followed by measurement of absorbance at 660 nm after standing at room temperature for 20 minutes to detect production of potassium ferricyanide. The activity of the enzyme which produces 1 µmol of potassium ferricyanide by oxidizing 1 µmol of D-arabitol in one minute under the present reaction conditions was defined as 1 unit. As a result of the measurement of D-arabitol dehydrogenase activity by the present method, an activity of 1.46 unit/mg protein was detected.

EXAMPLE 3

Oxidation Reaction of D-arabitol Using a Cell Homogenate Prepared from *Gluconobacter oxydans* ATCC261 Cells Oxidation reaction of D-arabitol was performed using a cell homogenate prepared from *Gluconobacter oxydans* ATCC261 cells in the same manner as in Example 2. The oxidation reaction of D-arabitol was carried out in 1 ml of a reaction mixture containing 1% (w/v) D-arabitol, 0.1 M sodium acetate buffer solution (pH 5.0) and 0.1 ml of a cell homogenate. While the reaction mixture was being shaken mildly at pH 5.0 and at 25° C., the reaction was continued for 24 hours. After completion of the reaction, the reaction product was analyzed by HPLC, which indicated complete consumption of D-arabitol and production and accumulation of 0.88% (w/v) D-xylose and 0.05% xylitol.

EXAMPLE 4

Detection of D-xylulose Reductase Activity in *Gluconobacter oxydans*

About 1.0 g in wet weight of cultivated cells of *Gluconobacter oxydans* ATCC621 prepared in the same manner as in Example 2 were suspended in 10 ml of a 0.1 M phosphate buffer solution (pH 7.0) and sonicated at 4° C. for 20 minutes to prepare a cell homogenate. The homogenate was centrifuged (at 8,000 rpm, for 10 minutes) to remove cell debris to prepare a cell-free extract.

According to the method of Kersters et al. (*Meth. Enzymol.*, 9 (1966) 170), the activity of D-xylulose reductase which require NADH or NADPH as a coenzyme was measured by xylitol dehydrogenation reaction, which is a reverse reaction of xylitol production reaction. The reaction was carried out in 1 ml of a reaction mixture containing 2 mM NAD or NADP, 100 mM xylitol, 100 mM Trishydrochloride buffer solution (pH 8.0) and 50 µl of a cell-free extract at pH 8.0 and at 30° C. for 10 minutes. The reaction was proceeded in a cuvette, and a change in absorbance at 340 nm was measured continually. The production of NADH or NADPH was detected by an increase in absorbance at 340 nm. The activity of the enzyme which produces 1 µmol of NADH or NADPH by oxidizing 1 µmol of xylitol in one minute under the present reaction conditions was defined as 1 unit.

As a result, when NAD was added as a coenzyme, a high activity of 2.57 units/mg protein was detected. On the other hand, when NADP(H) was added, no activity was detected, which indicated that NADPH did not act as a coenzyme.

EXAMPLE 5

Reduction Reaction of D-xylulose Using a Cell-free Extract Prepared from *Gluconobacter oxydans* ATCC621 cells A cell-free extract was prepared from *Gluconobacter oxydans* ATCC621 cells in the same manner as in Example 4. This cell-free extract was dialyzed against 2L of 0.1 M phosphate buffer to remove low molecular weight compounds. Reduction reaction of D-xylulose was carried out using the cell-free extract. The reduction reaction of D-xylulose was carried out in 1 ml of a reaction mixture containing 1% (w/v) D-xylulose, 0.1 M sodium acetate buffer solution (pH 5.0), each coenzyme in a concentration shown in Table 1, and 0.1 ml of the cell-free extract. While the reaction mixture was being shaken mildly at pH 5.0 and at 30° C., the reaction was continued for 24 hours. After completion of the reaction, the bacterial cells were removed by centrifugation, the reaction product was analyzed by HPLC.

As the results shown in Table 1, production of xylitol was detected only when NADH was added. The amount of xylitol produced depended on the amount of NADH added, and xylitol was produced in an approximately equimolar amount with respect to the NADH added.

TABLE 1

Amount of xylitol produced by reduction reaction of D-xylulose using a cell-free extract prepared from Gluconobacter oxydans ATCC621 cells

| Coenzyme added | Concentration added (mM) | Xylitol produced (%(w/v)) | Xylitol produced (mM) |
| --- | --- | --- | --- |
| None | 0 | Not detected | — |
| NADH | 5 | 0.07 | 4.6 |
| NADH | 10 | 0.15 | 9.9 |
| NADH | 15 | 0.21 | 13.8 |
| NADPH | 5 | Not detected | — |
| NAD | 5 | Not detected | — |
| NADP | 5 | Not detected | — |

EXAMPLE 6

Effect of Addition of Glucose and Ethanol in Conversion Reaction from D-arabitol to Xylitol by *Gluconobacter oxydans* ATCC621 Cells 50 ml of a culture medium (pH7.0) containing 2.4% (w/v) of potato dextrose (manufactured by Difco), 3% of yeast extract (Difco), 0.5% of meat extract (Difco), and 1.5% of glycerol was dispensed in 500 ml Sakaguchi flasks and sterilized at 120° C. for 15 minutes. After a D-arabitol solution was sterilized at 120° C. for 15 minutes, it was added to the above-described culture medium to a concentration of 3.0%. Further, 1 g of calcium carbonate, after sterilized at 200° C. for 120 minutes, was added to the culture medium described above. *Gluconobacter oxydans* ATCC621 was inoculated to this culture medium and cultivated with shaking at 30° C. for 3 days. The bacterial cells were collected from the culture solution by centrifugation and washed once with physiological saline.

D-arabitol was dissolved in 0.1M phosphate buffer solution(pH 6.0) to a final concentration of 5.24% (w/v), and 10 ml each of the solution was dispensed in test tubes. To this reaction mixture were added the bacterial cells in a wet weight of about 10% (w/v) and 2% (w/v) of calcium carbonate for the purpose of preventing a decrease in pH at the time of reaction, and a reaction with shaking was run at 30° C. In the lot where a carbon source was added, 1% (w/v) glucose was added at the initiation of the reaction and 5% (v/v) ethanol was added after 6 hours from the initiation of the reaction for further reaction. Each 1-ml sample was taken after 6, 24, and 48 hours from the initiation of the reaction. After removing the bacterial cells by centrifugation, the reaction product was analyzed by HPLC.

Figure 2A:
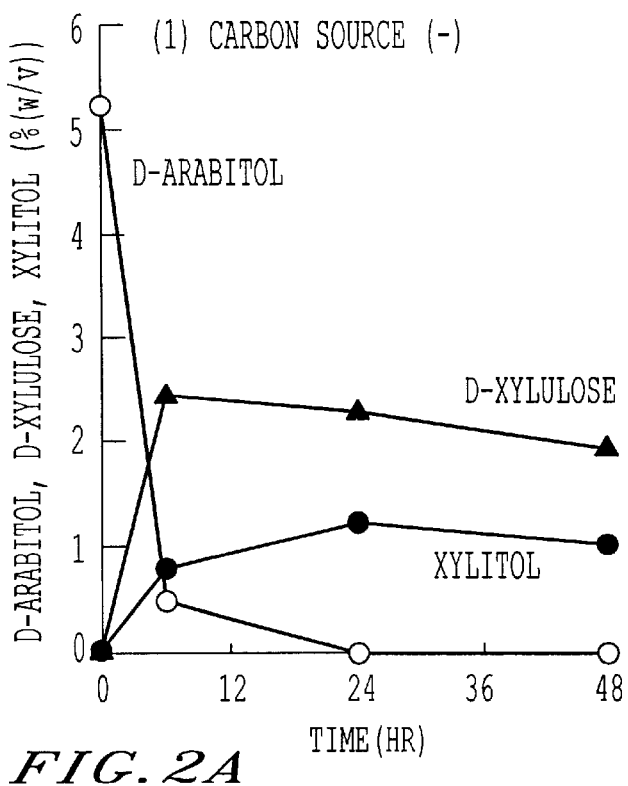
FIG. 2 is a graph illustrating a time-course of a conversion reaction from D-arabitol to xylitol by *Gluconobacter oxydans* ATCC621 cells without addition of any carbon source or with addition of glucose and ethanol.
Figure 2B:
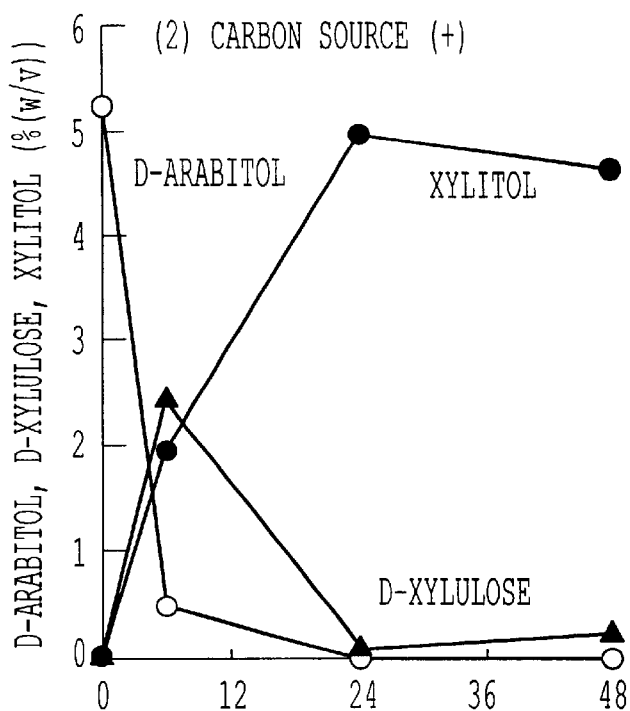

As illustrated in FIG. 2, addition of glucose and ethanol resulted in the production of an significantly increased amount of xylitol, so that a considerable effect of their addition was observed. In the case where no carbon source was added, D-arabitol was oxidized substantially completely to D-xylulose. Even in the reaction without addition of any carbon source, prevention of pH at the time of reaction from decreasing by addition of calcium carbonate resulted in a slight increase in the yield of xylitol, more particularly 1.23% (w/v) xylitol was produced in 24 hours' reaction. However, a portion of D-xylulose remained unreacted, no further increase in yield did occur. In contrast, with addition of a carbon source, D-xylulose was reduced to xylitol substantially completely, and at the point in time of 24 hours, xylitol was produced and accumulated in a yield as high as 5.24% (w/v) (98% based on D-arabitol).

EXAMPLE 7

Effect of Addition of a Sugar and a Sugar Alcohol in the Conversion Reaction from D-arabitol to Xylitol by *Gluconobacter oxydans* ATCC621 Cells D-arabitol was dissolved in 0.1M phosphate buffer solution(pH 6.0) to a final concentration of 5% (w/v), and 5 ml each of the solution was dispensed in a test tube. To this reaction mixture were added the bacterial cells prepared in the same manner as in Example 6 in a wet weight of about 10% (w/v) and 2% (w/v) of calcium carbonate, and a reaction with shaking was run at 30° C. After 6 hours' reaction, 5% (w/v) of various sugars and sugar alcohols were added as shown in Table 2 for further reaction. After the reaction was continued for 27 hours, the bacterial cells were removed by centrifugation and then the amount of xylitol produced was determined by HPLC. As shown in Table 2, an increase in the amount of xylitol produced was recognized by addition of various sugars and sugar alcohols.

TABLE 2

Effect of addition of sugars and sugar alcohols in the production reaction of xylitol

| Carbon source added | Amount of xylitol produced (%(w/v)) |
| --- | --- |
| None | 1.7 |
| D-Glucose | 4.5 |
| D-Fructose | 2.81 |
| D-Sorbitol | 2.62 |
| Glycerol | 3.08 |

EXAMPLE 8

Effect of Addition of Organic Acids and Alcohols in the Conversion Reaction from D-arabitol to Xylitol by *Gluconobacter oxydans* ATCC621 Cells D-arabitol was dissolved in 0.1M phosphate buffer solution(pH 6.0) to a final concentration of 5% (w/v), and 5 ml each of the solution was dispensed in a test tube. To this reaction mixture were added the bacterial cells prepared in the same manner as in Example 6 in a wet weight of about 10% (w/v) and 2% (w/v) of calcium carbonate, and a reaction with shaking was run at 30° C. After 6 hours and 10 hours from the initiation of the reaction, 5% (w/v) formic acid, acetic acid, gluconic acid, or citric acid, or 1% (v/v) methanol, ethanol, or propanol was added for further reaction. After the reaction was continued for 27 hours, the bacterial cells were removed by centrifugation and then the amount of xylitol produced was determined by HPLC. As shown in Table 3, an increase in the amount of xylitol produced was recognized by addition of various organic acids and alcohols.

TABLE 3

Effect of addition of organic acids or alcohols in the production reaction of xylitol

| Carbon source added | Amount of xylitol produced (%(w/v)) |
| --- | --- |
| None | 1.7 |
| Formic acid | 2.63 |
| Acetic acid | 2.43 |
| Gluconic acid | 2.23 |
| Citric acid | 2.44 |
| Methanol | 1.9 |
| Ethanol | 3.31 |
| Propanol | 2.98 |

EXAMPLE 9

Production of Xylitol by Cell Reaction of *Acetobacter xlinum* ATCC14851

Forty ml of a culture medium (pH7.0) containing 2.4% (w/v) of potato dextrose (manufactured by Difco), 3% of yeast extract (Difco), 0.5% of meat extract (Difco), and 1.5% of glycerol was dispensed in 500 ml Sakaguchi flasks and sterilized at 120° C. for 15 minutes. After solutions containing D-arabitol, xylitol and D-xylulose, respectively, were sterilized at 120° C. for 15 minutes, they were added to the above-described culture medium to a concentration of 2.0%, 1.0%, and 1.0%, respectively. Further, 1 g of calcium carbonate, after sterilized at 200° C. for 120 minutes, was added to the culture medium described above. *Acetobacter xylinum* ATCC14851 was inoculated to this culture medium and cultivated with shaking at 30° C. for 3 days. The bacterial cells were collected from the culture solution by centrifugation and washed once with physiological saline.

D-arabitol and D-glucose were dissolved in 0.1M phosphate buffer solution(pH 6.0) to final concentrations of 5% (w/v) and 1% (w/v), respectively, and 5 ml each of the solution was dispensed in a test tube. The bacterial cells in a wet weight of about 10% (w/v) and 2% (w/v) of calcium carbonate were added to this reaction mixture, and a reaction with shaking was run at 30° C. In the lot where a carbon source was added, 1% (w/v) glucose was added at the initiation of the reaction and 5% (v/v) ethanol was added after 6 hours from the initiation of the reaction for further reaction. The reaction was stopped after 24 hours from the initiation thereof. After the bacterial cells were removed by centrifugation, the reaction product was analyzed by HPLC. In the case where no carbon source was added, a portion of D-xylulose remained unreacted and the amount of xylitol produced was 0.98% (w/v) (yield of 20% based on D-arabitol) whereas in the case where a carbon source was added, the efficiency of conversion reaction was increased and xylitol was produced and accumulated in a yield as high as 2.57% (w/v) (yield of 51% based on D-arabitol).

Industrial Applicability

The present invention enables producing xylitol by a simple process using D-arabitol as a starting material.

What is claimed is:

1. A method for producing xylitol comprising the step of reacting a microorganism having an ability to convert D-arabitol to xylitol with D-arabitol to product xylitol,
   wherein said microorganism is a microorganism which has an ability to metabolizing a carbon source to produce NADH, and the carbon source is added to a reaction system.

2. The method as claimed in claim 1, wherein said microorganism has an D-arabitol dehydrogenase activity and D-xylulose reductase (xylitol dehydrogenase) activity.

3. The method as claimed in claim 1, wherein said microorganism is a microorganism which belongs to the genus Gluconobacter or Acetobacter.

4. The method as claimed in claim 3, wherein said microorganism belonging to the genus Gluconobacter or Acetobacter is *Gluconobacter oxydans* or *Acetobacter xylinum*.

5. The method as claimed in claim 3, wherein the carbon source to be added to the reaction system is selected from the group consisting of sugars, sugar derivatives, alcohols, aldehydes, organic acids, and mixtures thereof.

6. The method as claimed in claim 5, wherein said sugars, sugar derivatives, alcohols, aldehydes, and organic acids are selected from the group consisting of glucose, fructose, sucrose, lactose, sorbitol, glycerol, gluconic acid, methanol, ethanol, propanol, isopropyl alcohol, 1,4-butanediol, 2,3-butanediol, formaldehyde, acetaldehyde, propionaldehyde, isobutyraldehyde, glyceraldehyde, formic acid, acetic acid, citric acid, fumaric acid, malic acid, and mixtures thereof.

7. A method for producing xylitol comprising the step of reacting a microorganism having an ability to convert D-arabitol to xylitol with D-arabitol to produce xylitol,
   wherein said microorganism is a preparation product of cells of the microorganism, and NADH is added to a reaction system.

8. The method as claimed in claim 7, wherein said microorganism has an D-arabitol dehydrogenase activity and D-xylulose reductase (xylitol dehydrogenase) activity.

9. The method as claimed in claim 7, wherein said microorganism is a microorganism which belongs to the genus Gluconobacter or Acetobacter.

10. The method as claimed in claim 9, wherein said microorganism belonging to the genus Gluconobacter or Acetobacter is *Gluconobacter oxydans* or *Acetobacter xylinum*.

* * * * *